(12) United States Patent
Benner et al.

(10) Patent No.: US 8,389,703 B1
(45) Date of Patent: *Mar. 5, 2013

(54) RIBONUCLEOSIDE ANALOGS WITH NOVEL HYDROGEN BONDING PATTERNS

(76) Inventors: Steven A. Benner, Gainesville, FL (US); Hyo-Joong Kim, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/287,169

(22) Filed: Nov. 2, 2011

Related U.S. Application Data

(63) Continuation-in-part of application No. 11/372,400, filed on Mar. 9, 2006, now Pat. No. 8,053,212, which is a continuation-in-part of application No. 11/212,230, filed on Aug. 27, 2005, now abandoned.

(60) Provisional application No. 60/605,061, filed on Aug. 28, 2004, provisional application No. 60/614,413, filed on Sep. 29, 2004, provisional application No. 60/617,636, filed on Oct. 13, 2004.

(51) Int. Cl.
*C07H 19/048* (2006.01)
*C07H 21/00* (2006.01)
*C07H 21/02* (2006.01)

(52) U.S. Cl. ............... 536/23.1; 536/25.34; 536/28.1

(58) Field of Classification Search .................. None
See application file for complete search history.

(56) References Cited

U.S. PATENT DOCUMENTS

| | | | | |
|---|---|---|---|---|
| 5,432,272 A | * | 7/1995 | Benner | 536/25.3 |
| 6,001,983 A | * | 12/1999 | Benner | 536/23.1 |
| 6,140,496 A | * | 10/2000 | Benner | 536/27.1 |
| 6,627,456 B1 | * | 9/2003 | Benner | 436/501 |
| 8,053,212 B1 | * | 11/2011 | Benner | 435/91.1 |

OTHER PUBLICATIONS

Hutter and Benner, "Expanding the Genetic Alphabet: Non-Epimerizing Nucleoside with the pyDDA Hydrogen Bonding Pattern," Journal of Organic Chemistry, 68(25), 9839-9842 (2003); WEB publ. Nov. 13, 2003).*

Yang et al., "Artificially Expanded Genetic Information System: A New Base Pair with Alternative Hydrogen Bonding Pattern," Nucleic Acids Research, 34(21), 6095-6101 (2006); WEB publ. Oct. 29, 2006).*

Watanabe et al., "Novel Ring Transformation Reactions and Their Applications to the Synthesis of Potential Anticancer Heterocyclic Compounds," Heterocycles. 21(1), 289-307 (1984).*

Sheng, P. P., Yang, Z. Y., Kim, Y. M., Wu, Y. R., Tan, W. H., Benner, S. A. (2008) Design of a novel molecular beacon. Modification of the stem with artificially genetic alphabet. Chem. Comm. (41), 5128-5130.

Yang, Z., Sismour, A. M., Sheng, P., Puskar, N. L., Benner, S. A. (2007) Enzymatic incorporation of a third nucleobase pair. Nucl. Acids Res. (35), 4238-4249.

Yang, Z., Chen, F., Chamberlin, S. G., Benner, S. A. (2010) Expanded genetic alphabets in the polymerase chain reaction. Agnew. Chem. (49). 177-180.

Robbins, D. J., Barkley, M. D., Coleman, M. S. (1987) Interaction of terminal transferase with single-stranded DNA. J of Biol. Chem. (262), 9494-9502.

Von Krosigk, U., Benner, S. A. (1995) pH-independent triple helix formation by an oligonucleotide containing a pyrazine donor-donor-acceptor base. J. Am. Chem. Soc. (117), 5361-5362.

Voegel, J. J., Benner, S. A. (1994) Non-standard hydrogen bonding in duplex oligonucleotides. The base pair between an acceptor-donor-donor pyrimidine analog and a donor-acceptor-acceptor purine analog. J. Am. Chem. Soc. (116), 6929-6930.

Bain, J. D., Chamberlin, A. R., Switzer, C. Y., Benner, S. A. (1992) Ribosome-mediated incorporation of non-standard amino acids into a peptide through expansion of the genetic code. Nature (356), 537-539.

Dellinger, D. J., Timar, Z., Myerson, J., Sierzchala, A. B., Turner, J., Fereira, F., Kupihar, Z., Dellinger, G., Hill, K. W., Powell, J. A., Sampson, J. R., Caruther, M. H. (2011) Streamlined process for the chemical synthesis of RNA using 2'-O-thionocarbamate-protected nucleoside phosphoramidites in the solid phase. J. Am. Chem. Soc. (133) 11540-11556.

Elbeik, T., Surithade, J., Destree, M., Gorlin, J., Holodniy, M., Jortani, S. A., Kuramoto, K, Ng, V., Valdes, R., Valasamakis, A., Terrault, N. A. (2004) Multicenter evaluation of the performance characteristics of the Bayer VERSANT HCV RNA 3.0 assay (bDNA). J. Clin. Microbiol. (42) 563-569.

Elbeik, T., Markowitz, N., Nassos, P., Kumar, U., Beringer, S., Haller, B., Ng, V. (2004) Simultaneous runs of the Bayer VERSANT HIV-1 version 3.0 and HCV bDNA version 3.0 quantitative assays on the system 340 platform provide reliable quantitation and improved work flow. J. Clin. Microbial., (42), 3120-3127.

Ireland, R. E., Thausnvongs, S., Vanier, N, Wilcox, C. S. (1980) Enolate claisen rearrangements of esters from furanoid and pyranoid glycols. J. Org. Chem. (45) 48-61.

Walker, J. A. II, Chen, J. J., Wise, D. S., Townsend, L. B. (1996) A facile, multigram synthesis of ribofuranoid glycols. J. Org. Chem. (61), 2219-2221.

Cameron, M. A., Cush, S. B., Hammer, R. P. (1997) Facile preparation of protected funanoid glycals from thymidine. J. Org. Chem. (62) 9065-9069.

* cited by examiner

*Primary Examiner* — Lawrence E Crane

(57) ABSTRACT

This invention relates to nucleoside, nucleotide, and oligonucleotide analogs that incorporate non-standard nucleobase analogs, defined to be those that present a pattern of hydrogen bonds to a paired nucleobase analog in a complementary strand that is different from the pattern presented by adenine, guanine, cytosine, and thymine. The invention is specifically concerned with nucleotide analogs that present the donor-donor-acceptor, hydrogen bonding patterns on pyrimidine analogs, and especially those that are analogs of ribonucleotides, including protected ribonucleotides suitable for phosphoramidite-based synthesis of RNA. The heterocycles on these nucleoside analogs are aminopyridones that have electron withdrawing groups attached to the position analogous to the 5-position of the ring in standard pyrimidines, including nitro, cyano, and carboxylic acid derivatives.

11 Claims, 5 Drawing Sheets

Figure 2

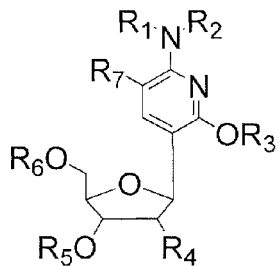

$R_5$ = phosphoramidite, P(O-beta-cyanoethyl)NX$_2$
$R_6$ = protecting group. e.g. trityl, methoxytrityl, dimethoxytrityl, trimethoxytrityl
$R_7$ = CN, NO$_2$, COOX, CONHX $R_1$ = —H
$-\overset{O}{\underset{}{C}}X$
X=C$_1$~C$_{12}$ linear or branched alkyl, allyl, benzyl, phenyl $R_2$ = —H
$-\overset{O}{\underset{}{C}}X$
X=C$_1$~C$_{12}$ linear or branched alkyl, allyl, benzyl, phenyl $R_3$ = —H
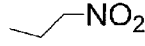
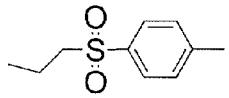
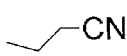
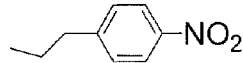

$R_1, R_2 = \overset{X_1}{\underset{}{=}}\overset{}{\underset{N}{}}\overset{X_2}{\underset{X_3}{}}$   $X_1$ = H, C$_1$~C$_{12}$ linear or branched alkyl
$X_2$ = C$_1$~C$_{12}$ linear or branched alkyl
$X_3$ = C$_1$~C$_{12}$ linear or branched alkyl $R_4$ = —OH
$-O\overset{allyl}{}$
—OCH$_3$
$-O\overset{CH_3}{\underset{CH_3}{Si}}$Bu

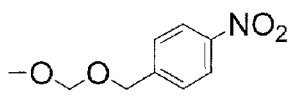
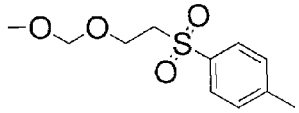
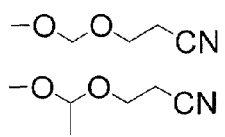

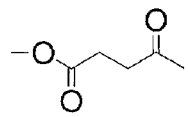
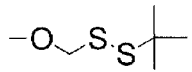
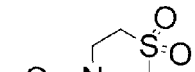

US 8,389,703 B1

RIBONUCLEOSIDE ANALOGS WITH NOVEL HYDROGEN BONDING PATTERNS

CROSS REFERENCE TO RELATED APPLICATIONS

This application is a continuation-in-part of the U.S. patent application Ser. No. 11/372,400, filed Mar. 9, 2006, and issued Nov. 8, 2011 as U.S. Pat. No. 8,053,212; which is a continuation-in-part of U.S. patent application Ser. No. 11/212,230, filed Aug. 27, 2005, now abandoned, which claims priority benefits as a continuation-in-part of U.S. Provisional Applications U.S. 60/605,061, filed Aug. 28, 2004, U.S. 60/614,413, filed Sep. 29, 2004, and U.S. 60/617,636, filed Oct. 13, 2004.

STATEMENT OF RIGHTS TO INVENTIONS MADE UNDER FEDERALLY-SPONSORED RESEARCH

This invention was made with government support under HG004647 awarded by NIH. The government has certain rights in the invention.

NAMES OF THE PARTIES TO A JOINT RESEARCH AGREEMENT

Not applicable.

INCORPORATION-BY-REFERENCE OF MATERIAL SUBMITTED ON A DISC

None.

FIELD OF INVENTION

This invention relates to the field of nucleic acid chemistry, more specifically to nucleic acid analogs, and still more specifically to analogs that, when incorporated into oligonucleotides, present to a complementary strand in a Watson-Crick pairing geometry a pattern of hydrogen bonds that is different from the pattern presented by adenine, guanine, cytosine, and uracil. Most specifically, this invention enables the synthesis of and claims compositions of matter that present the donor-donor-acceptor, donor-acceptor-donor, and acceptor-donor-donor non-standard hydrogen bonding patterns on pyrimidine nucleoside analogs on a ribose-like sugar backbone.

BACKGROUND

Natural oligonucleotides bind to complementary oligonucleotides (DNA and RNA, collectively xNA) according to the well-known rules of nucleobase pairing first elaborated by Watson and Crick, under which adenine (A) pairs with thymine (T) (or uracil, U, in RNA), and guanine (G) pairs with cytosine (C), with the complementary strands anti-parallel to one another. These pairing rules allow for the specific hybridization of an oligonucleotide to a complementary oligonucleotide; this oligonucleotides valuable as probes in the laboratory, in diagnostic applications, as messages that can direct the synthesis of specific proteins, and for a wide range of other applications. Such base pairing is used, for example and without limitation, to capture other oligonucleotides to beads, arrays, and other solid supports, to allow nucleic acids to fold in hairpins, beacons, and catalysts, as supports for functionality, such as fluorescence, fluorescence quenching, binding/capture tags, and catalytic functionality, as part of more complex architectures, including dendrimers and nanostructures, and as scaffolds to guide chemical reactions. When the oligonucleotide is a ribonucleotide, then it can serve as a message to guide the ribosome to synthesize proteins.

Further, nucleobase pairing is used by enzymes to catalyze the synthesis of new oligonucleotides that are complementary to template nucleotides. In this synthesis, building blocks (normally the triphosphates of ribo- or deoxyribonucleosides carrying of A, T, U, C, or G) are directed by a template oligonucleotide to form a complementary oligonucleotide with the complementary sequence. This process is the basis for replication of all forms of life, and also serves as the basis for technologies for enzymatic synthesis and amplification of specific heterosequence nucleic acids by enzymes such as DNA and RNA polymerases, in the polymerase chain reaction (PCR) [Yang, Z., Chen, F., Alvarado, J. B., Benner, S. A. (2011) Amplification, mutation, and sequencing of a six-letter synthetic genetic system. *J. Am. Chem. Soc.* 133, 15105-15112], and in a variety of architectures that may involve synthesis, ligation, cleavage, immobilization and release, inter alia, used in technology to detect nucleic acids.

Nucleobase pairing is useful in many architectures. In solution, nucleobase pairing in the loop of a molecular beacon can open the beacon, separating a fluorescent species attached to one end of a hairpin structure from a quencher on the other [Sheng, P. P., Yang, Z. Y., Kim, Y. M., Wu, Y. R., Tan, W. H. Benner, S. A. (2008) Design of a novel molecular beacon. Modification of the stem with artificially genetic alphabet. *Chem. Comm.* (41), 5128-5130]. Pairing can assemble two DNA fragments transiently or covalently, as in a template-directed ligation. Pairing is useful for affixing an oligonucleotide that is free in solution to a support carrying the complementary oligonucleotide. The oligonucleotide can carry functional groups, including fluorescent groups attached to the nucleobases.

The Watson-Crick pairing rules can be understood chemically in terms of the arrangement of hydrogen bonding groups on the heterocyclic nucleobases of the oligonucleotide, groups that can either be hydrogen bond donors or acceptors. In the standard Watson-Crick geometry, a large purine nucleobase pairs with a small pyrimidine nucleobase. Thus, the A:T nucleobase pair is essentially the same size as a G:C nucleobase pair. This means that the rungs of the DNA ladder, formed from either AT or GC nucleobase pairs, all have the same length.

Further recognition between nucleobases is determined by hydrogen bonds between the nucleobases. In standard nucleobases, hydrogen bond donors are heteroatoms (nitrogen or oxygen in the natural nucleobases) bearing a hydrogen; hydrogen bond acceptors are heteroatoms (nitrogen or oxygen in the natural nucleobases) with a lone pair of electrons. In the geometry of the Watson-Crick nucleobase pair, a six membered ring (in standard nucleobases, a pyrimidine) is juxtaposed to a ring system composed of a fused six membered ring and a five membered ring (in standard nucleobases, a purine), with a middle hydrogen bond linking two ring atoms, and hydrogen bonds on either side joining functional groups appended to each of the rings, with donor groups paired with acceptor groups.

In many applications, the nucleobases incorporated into one or more oligonucleotide analogs carry an appendage. In standard nucleobases, the appendage, or side chain, is attached to one or more pyrimidines at the 5-position, or at the 7-position of a 7-deazapurine, or to an exocyclic nitrogen, most often the exocyclic amino group of adenine or cytosine. Such nucleoside analogs have application because of their combination of Watson-Crick nucleobase pairing ability and the properties or reactivities associated with species appended via the side chain. For example, oligonucleotides containing a T to which is appended a side chain bearing a biotin residue can first bind to a complementary oligonucleotide, and the hybrid can then be isolated by virtue of the specific affinity of biotin to avidin [Langer, P. R.; Waldrop, A. A.; Ward, D.C. (1981) *Proc. Nat. Acad. Sci.* 78, 6633-6637]. This finds application in diagnostic work. Instead of biotin, the side chain can carry a fluorescent moiety, or a moiety that quenches the fluorescence of another moiety, a branching point, or a moiety that complexes to a metal, or a moiety that confers catalytic activity on the oligonucleotide, or a moiety that assists in the attachment of the oligonucleotide analog to a solid support, such as a bead, a one dimensional array, or a two dimensional array.

Often, derivatized standard nucleotides can be incorporated into oligonucleotides by enzymatic transcription of natural oligonucleotide templates in the presence of the triphosphate of the derivatized nucleoside, the substrate of the appropriate (DNA or RNA) polymerase, or a reverse transcriptase. In this process, a natural nucleoside is placed in the template, and standard Watson-Crick pairing is exploited to direct the incoming modified nucleoside opposite to it in the growing oligonucleotide chain.

The standard available nucleobase pairs are limited in that they make available only two mutually exclusive hydrogen bonding patterns. This means that should one wish to introduce a modified nucleoside based on one of the natural nucleosides into an oligonucleotide, it would be incorporated wherever the complementary natural nucleoside is found in the template. For many applications, this is undesirable.

Further, in many applications, it would be desirable to have extra nucleobase pairs that behave as predictably as the AT (or U) and GC nucleobase pairs, but that do not cross-pair with natural oligonucleotides, which are built from A, T (or U), G, and C. This is especially true in diagnostics assays based. Biological samples generally contain many nucleic acid molecules in addition to the nucleic acid that one wishes to detect. The adventitious DNA/RNA, often present in abundance over the targeted analyte DNA (or RNA), is also composed of A, T (or U), G, and C. Thus, adventitious DNA/RNA can compete with the desired interactions between two or more oligonucleotide-like molecules. Many seek RNA molecules with nucleotides in addition to the standard A, U, C and G to encode proteins with more than the 20 standard amino acids [Bain, J. D., Chamberlin, A. R., Switzer, C. Y., Benner, S. A. (1992) Ribosome-mediated incorporation of non-standard amino acids into a peptide through expansion of the genetic code. *Nature* 356, 537-539].

Many limitations that arise from the existence of only four standard nucleobases joined in only two types of nucleobase pairs via only two types of hydrogen bonding schemes, could be overcome were additional nucleobases available that could be incorporated into oligonucleotides by chemical synthesis or enzymatically. Here, the additional nucleobases would still pair in the Watson-Crick geometry, but would present patterns of hydrogen bond donating and accepting groups in a pattern different from those presented by the natural nucleobases. They therefore would form nucleobase pairs with additional complementary nucleobases in preference to (and, preferably, with strong preference to, meaning with at least a 10 to 100 fold affinity greater than to mismatched oligonucleotides or oligonucleotide analogs).

Over the past two decades, Benner disclosed compositions of matter that were intended to overcome the limitations of molecular recognition by changing the pattern of hydrogen bond donor and acceptor groups presented by a nucleobase to the nucleobase on a complementary oligonucleotide analog [U.S. Pat. Nos. 5,432,272, 5,965,364, 6,001,983, 6,037,120, 6,140,496, 6,627,456, 6,617,106]. These disclosures showed that the geometry of the Watson-Crick nucleobase pair can accommodate as many as twelve nucleobases forming six mutually exclusive pairs. Of these, four nucleobases forming two pairs are "standard", while eight nucleobases forming four pairs were termed "non-standard".

Adding the non-standard nucleobases to the standard nucleobases yielded an Artificially Expanded Genetic Information System (AEGIS). Specifically, the structures shown in FIG. 1, taken from U.S. Pat. No. 6,140,496, implement the designated hydrogen bonding patterns. It was also noted that these nucleobases analogs might be functionalized to enable a single biopolymer capable of both genetics and catalysis. Expanded genetic alphabets have now been further explored in a variety of laboratories, and the possibility of a fully artificial genetic system has been advanced [Switzer, C. Y., Moroney, S. E., Benner, S. A. (1989) Enzymatic incorporation of a new base pair into DNA and RNA. *J. Am. Chem. Soc.* 111, 8322-8323] [Piccirilli, J. A., Krauch, T., Moroney, S. E., Benner, S. A. (1990) Extending the genetic alphabet. Enzymatic incorporation of a new base pair into DNA and RNA. *Nature* 343, 33-37] [Piccirilli, J. A., Krauch, T., MacPherson, L. J., Benner, S. A. (1991) A direct route to 3-(ribofuranosyl)-pyridine nucleosides. *Helv. Chim. Acta* 74, 397-406] [Voegel, J. J., Altorfer, M. M., Benner, S. A. (1993) The donor-acceptor-acceptor purine analog. Transformation of 5-aza-7-deaza-isoguanine to 2'-deoxy-5-aza-7-deaza-iso-guanosine using purine nucleoside phosphorylase. *Helv. Chim Acta* 76, 2061-2069] [Voegel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547] [Heeb, N. V., Benner, S. A. (1994) Guanosine derivatives bearing an $N^2$-3-imidazolepropionic acid. *Tetrahedron Lett.* 35, 3045-3048] [Voegel, J. J., Benner, S. A. (1994) Non-standard hydrogen bonding in duplex oligonucleotides. The base pair between an acceptor-donor-donor pyrimidine analog and a donor-acceptor-acceptor purine analog. *J. Am. Chem. Soc.* 116, 6929-6930] [von Krosigk, U., Benner, S. A. (1995) pH-independent triple helix formation by an oligonucleotide containing a pyrazine donor-donor-acceptor base. *J. Am. Chem. Soc.* 117, 5361-5362] [Voegel, J. J., Benner, S. A. (1996) Synthesis, molecular recognition and enzymology of oligonucleotides containing the non-standard base pair between 5-aza-7-deaza-iso-guanine and 6-amino-3-methylpyrazin-2-one, a donor-acceptor-acceptor purine analog and an acceptor-donor-donor pyrimidine analog. *Helv. Chim. Acta* 79, 1881-1898] [Voegel, J. J., Benner, S. A. (1996) Synthesis and characterization of non-standard nucleosides and nucleotides bearing the acceptor-donor-donor pyrimidine analog 6-amino-3-methylpyrazin-2-one. *Helv. Chim. Acta* 79, 1863-1880] [Kodra, J., Benner, S. A. (1997) Synthesis of an N-alkyl derivative of 2'-deoxyisoguanosine. *Syn. Lett.*, 939-940] [Jurczyk, S., Kodra, J. T., Rozzell, J. D., Jr., Benner, S. A., Battersby, T. R. (1998) Synthesis of oligonucleotides containing 2'-deoxyisoguanosine and 2'-deoxy-5-methyliso-cytidine using phosphoramidite chemistry. *Helv. Chim. Acta* 81, 793-811] [Lutz, S., Burgstaller, P., Benner, S. A. (1999) An in vitro screening technique for polymerases that can incorporate modified nucleotides. Pseudouridine as a substrate for thermostable polymerases. *Nucl. Acids Res.* 27, 2792-2798] [Jurczyk, S. C., Battersby, T. R., Kodra, J. T., Park, J.-H., Benner, S. A. (1999) Synthesis of 2'-deoxyisoguanosine triphosphate and 2'-deoxy-5-methyl-isocytidine triphosphate. *Helv. Chim. Acta.* 82, 1005-1015] [Jurczyk, S. C., Horlacher, J., Devine, K. G., Benner, S. A., Battersby, T. R. (2000) Synthesis and characterization of oligonucleotides containing 2'-deoxyxanthosine using phosphoramidite chemistry. *Helv. Chim. Acta* 83, 1517-1524] [Rao, P., Benner, S. A. (2001) A fluorescent charge-neutral analog of xanthosine: Synthesis of a 2'-deoxyribonucleoside bearing a 5-aza-7-deazaxanthine base. *J. Org. Chem.* 66, 5012-5015]

To systematize the nomenclature for the hydrogen bonding patterns, the hydrogen bonding pattern implemented on a small component of a nucleobase pair pare designated by the prefix "py". Following this prefix is the order, from the major groove to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Again following the prefix, the hydrogen bond donor and acceptor groups are designated, from the major to the minor grooves, using "A" and "D". Thus, the standard nucleobases adenine and guanine implement the standard hydrogen bonding patterns puDA- and puADD respectively.

A central teaching of this disclosure is that hydrogen bond patterns designated using this systematic nomenclature are distinct, in concept, from the organic molecules that are used to implement the hydrogen bonding pattern. Thus, guanosine is a nucleoside that implements the puADD hydrogen bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups. Which organic molecule is chosen to implement a specific hydrogen bonding pattern determines, in large part, the utility of the non-standard hydrogen bonding pattern, in various applications to which it might be applied.

The structures disclosed by U.S. Pat. No. 6,140,496, as well as its predecessor patents, provide for an expanded molecular recognition system by providing more than four independently recognizable building blocks that can be incorporated into DNA and RNA.

Should the additional nucleobase pairs be placed into DNA and RNA, and if once so placed they have the desirable pairing properties, chemical stability, and other features known to those skilled in they art, they could be useful for a variety of purposes. For example, RNA molecules prepared by transcription, although it is known to be a catalyst under special circumstances [Cech, T. R.; Bass, B. L (1986). *Ann. Rev. Biochem.* 55, 599] [Szostak, J. W. (1986) Nature 332, 83. Been, M. D.; Cech, T. R. (1988) *Science* 239, 1412], appear to have a much smaller catalytic potential than proteins because they lack building blocks bearing functional groups. Conversely, the limited functionality present on natural oligonucleotides constrains the chemist attempting to design catalytically active RNA molecules, in particular, RNA molecules that catalyze the template-directed polymerization of RNA.

Likewise, additional nucleobase pairs can be incorporated enzymatically at specific positions in an oligonucleotide molecule [Switzer, C. Y, Moroney, S. E., Benner, S. A. (1989) *J. Am. Chem. Soc.* 111, 8322]. If functionalized, such additional nucleobases should also allow the incorporation of functional groups into specific positions in a DNA or RNA sequence. A polymerase chain reaction has been demonstrated using a variant of an HIV reverse transcriptase to incorporate the pair between 2,4-diamino-5-(1'-beta-D-2'-deoxyribofuranosyl)-pyrimidine, implementing the pyDAD hydrogen bonding pattern, and 3,9-dihydro-9-(1'-beta-D-2'-deoxyribofuranosyl)-1H-purine-2,6-dione, implementing the puADA hydrogen bonding pattern [Sismour, A. M., Lutz, S., Park, J.-H., Lutz, M. J., Boyer, P. L., Hughes, S. H., Benner, S. A. (2004) PCR amplification of DNA containing non-standard base pairs by variants of reverse transcriptase from human immunodeficiency virus-1. *Nucl. Acids. Res.* 32, 728-735]. As standard nucleobases bearing functional groups at the 5-position of the uridine ring are accepted as substrates for most polymerases [Leary, J. L., Brigati, D. J., Ward, D. C. (1983) *Proc. Natl. Acad. Sci.* 80, 4045], non-standard nucleobases that are modified at the analogous positions are also accepted, provided that the polymerase accepts the parent non-standard nucleobase. New nucleobase pairs should also find use in studies of the structure of biologically important RNA and DNA molecules [Chen, T. R., Churchill, M. E. A. Tullius, T. D. Kallenbach, N. R., Seemann, N. C. (1988) *Biochem.* 27, 6032] and protein-nucleic acid interactions. They should also be useful in assembling nanostructures, including branched DNA useful for diagnostics, or for nanomachines. Further, non-standard nucleobases can be used to expand the genetic code, increasing the number of amino acids that can be incorporated translationally into proteins [Bain, J. D., Chamberlin, A. R., Switzer, C. Y., Benner, S. A. (1992) Ribosome-mediated incorporation of non-standard amino acids into a peptide through expansion of the genetic code. *Nature* 356, 537-539].

Many commercial applications have already been realized with the expanded genetic information systems disclosed by Benner in his patents. For example, the nucleobase pair between 2-amino-5-methyl]-(1'-beta-D-2'-deoxyribofuranosyl)-4(1H)-pyrimidinone, also known as 2'-deoxyisocytidine, disoC, or sometimes (less correctly) isoC and implementing the pyAAD hydrogen bonding pattern, and 6-amino-1,9-dihydro-9-(1'-beta-D-2'-deoxyribofuranosyl)-3H-purin-2-one, also known as 2'-deoxyisoguanosine, disoG, or sometimes (less correctly) isoG, and implementing the puDDA hydrogen bonding pattern, is incorporated into the branched DNA diagnostics tools marketed today by Siemens. Here, it provides molecular recognition on demand in aqueous solution, similar to nucleic acids but with a coding system that is orthogonal to the system in DNA and RNA [Elbeik, T., Surtihadi, J., Destree, M., Gorlin, J., Holodniy, M., Jortani, S. A., Kuramoto, K., Ng, V., Valdes, R., Valsamakis, A. Terrault, N. A. (2004) Multicenter evaluation of the performance characteristics of the Bayer VERSANT HCV RNA 3.0 assay (bDNA) *J. Clin. Microbiol.*, 42, 563-569] [Elbeik, T., Markowitz, N., Nassos, P., Kumar, U., Beringer, S., Haller, B. and Ng, V. (2004) Simultaneous runs of the Bayer VERSANT HIV-1 version 3.0 and HCV bDNA version 3.0 quantitative assays on the system 340 platform provide reliable quantitation and improved work flow. *J. Clin. Microbiol.*, 42, 3120-3127].

The Benner patents claimed a wide range of structures generally, but only a few specifically. The compounds specifically claimed, where those claims were supported by specific examples in the disclosure, were disclosed as the preferred implementations of the individual hydrogen bonding patterns, and are reproduced in FIG. 1 (taken from FIG. 2 of U.S. Pat. No. 6,140,496). Making reference to U.S. Pat. No. 6,140,496, the following implementations (where a systematic name is given for the 2'-deoxyribonucleoside; the corresponding ribonucleosides, 2'-O-methyl ribonucleosides, and various derivatives of these were also disclosed) were preferred as implementations for each of the hydrogen bonding patterns:

For the pyDAD hydrogen bonding pattern. The preferred embodiment disclosed in U.S. Pat. No. 6,140,496 supported the pyDAD hydrogen bonding pattern on the 2,4-diaminoypyrimidine heterocycle. The specific deoxyribonucleoside was 2,4-diamino-5-(1'-beta-D-2'-deoxyribofuranosyl)-pyrimidine, also named (1R)-1,4-anhydro-2-deoxy-1-C-(2,4-diamino-5-pyrimidinyl)-D-erythropentitol.

For the puADA hydrogen bonding pattern. The preferred embodiment disclosed in U.S. Pat. No. 6,140,496 supported the pyDAD hydrogen bonding pattern on the xanthine heterocycle. The specific deoxyribonucleoside was 3,9-dihydro-9-(1'-beta-D-2'-deoxyribofuranosyl)-1H-purine-2,6-dione, also known as 9-(2'-deoxy-beta-D-ribosyl)-xanthine.

For the pyAAD hydrogen bonding pattern. The preferred embodiment disclosed in U.S. Pat. No. 6,140,496 supported the pyDAD hydrogen bonding pattern on the 5-methyl-isocytosine heterocycle. The specific deoxyribonucleoside was 2-amino-5-methyl-1-(1'-beta-D-2'-deoxyribofuranosyl)-4(1H)-pyrimidinone, For the puDDA hydrogen bonding pattern. The preferred embodiment disclosed in U.S. Pat. No. 6,140,496 supported the pyDAD hydrogen bonding pattern on the isoguanine heterocycle. The specific deoxyribonucleoside was 6-amino-1,9-dihydro-9-(1'-beta-D-2'-deoxyribofuranosyl)-3H-purin-2-one.

For the pyDDA hydrogen bonding pattern. The preferred embodiment disclosed in U.S. Pat. No. 6,140,496 supported the pyDAD hydrogen bonding pattern on the 6-amino-5-methyl-2(1H)-pyrazinone heterocycle. The specific deoxyribonucleoside was 6-amino-5-methyl-3-(1'-beta-D-2'-deoxyribofuranosyl)-2(1H)-pyrazinone.

For the puAAD hydrogen bonding pattern. The preferred embodiment disclosed in U.S. Pat. No. 6,140,496 supported the pyDAD hydrogen bonding pattern on the 5-aza-3,7-dideazaguanosine heterocycle. The specific deoxyribonucleoside was 2-amino-1,9-dihydro-5-aza-3,7-dideaza-9-(1'-beta-D-2'-deoxyribofuranosyl)-1H-purin-6-one, also known as 7-amino-9-(1'-beta-D-2'-deoxyribofuranosyl)-imidazo[1,2-c]pyrimidin-5(1H)-one, For the pyADD hydrogen bonding pattern. The preferred embodiment disclosed in U.S. Pat. No. 6,140,496 supported the pyDAD hydrogen bonding pattern on the 6-amino-3-methyl-2(1H)-pyrazinone heterocycle. The specific deoxyribonucleoside was 6-amino-3-methyl-5-(1'-beta-D-2'-deoxyribofuranosyl)-2(1H)-pyrazinone, For the puDAA hydrogen bonding pattern. The preferred embodiment disclosed in U.S. Pat. No. 6,140,496 supported the pyDAD hydrogen bonding pattern on the 4-amino-1,3,5-triazin-2(8H)-one heterocycle. The specific deoxyribonucleoside was 4-amino-8-(2-deoxy-beta-D-erythro-pentofuranosyl)-imidazo[1,2-a]-1,3,5-triazin-2(8H)-one, also known as, 4-amino-8-(1'-beta-D-2'-deoxyribofuranosyl)-imidazo[1,2-a]-1,3,5-triazin-2(8H)-one.

Despite the value of the compositions disclosed by U.S. Pat. No. 6,140,496, it is clear that the specific compositions used to implement the various non-standard hydrogen bonding patterns were not optimal, at least from the perspective of potential utility. Several problematic physical and chemical properties of the compositions that were claimed specifically were disclosed in the specification of U.S. Pat. No. 6,140,496.

For example, the nucleobases that were, in U.S. Pat. No. 6,140,496, specifically disclosed as implementations of the pyADD and pyDDA hydrogen bonding patterns undergo an epimerization reaction that interconverts the beta and alpha anomers [von Krosigk, U., Benner, S. A. (1995) pH-independent triple helix formation by an oligonucleotide containing a pyrazine donor-donor-acceptor base. J. Am. Chem. Soc. 117, 5361-5362] [Vogel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. J. Org. Chem. 58, 7542-7547]. This is illustrated in FIG. 2. It was noted that this epimerization diminished the utility of these nucleobases. U.S. Pat. No. 6,140,496 and its predecessors proposed to solve the epimerization problem by replacing the furanose ring system (which includes an oxygen in a ring) with a carbocyclic cyclopentane derivative (which does not, and therefore cannot epimerize). The carbocyclic nucleoside analog is, however, difficult to synthesize, and has other disadvantages, and has never been incorporated into a commercial product.

An alternative tactic proposed to manage the epimerization problem has the pyrazine heterocycles that were the preferred implementations of the pyDDA and pyADD hydrogen bonding implementations (respectively) attached to a ribose derivative where a lower alkyl, most preferably methyl, group is attached to the 2'-oxygen. The 2'-O-alkyl group is large, and it was proposed that although the undesired epimerization reaction interconverting the beta and alpha anomers would still occur, steric factors would cause the beta (desired) form to predominate at equilibrium. Again, this would create problems if multiple non-standard nucleobases implementing this hydrogen bonding pattern were incorporated into an oligonucleotide analog.

Finally, although ribonucleoside derivatives were variously claimed in these patents, no synthetic schemes were provided to deliver them. Further, it was not obvious that the ribonucleosides suffered the same epimerization problem as the 2'-deoxyribosides, or that the epimerization problem can be mitigated by the heterocycles of the instant invention.

One purpose of the instant invention is to provide enabling and inventive procedures to prepare nucleoside analogs that implement the puAAD and pyDDA hydrogen bonding patterns, on a ribose sugar, as well as analogs where the 2'-oxygen of the sugar is irreversibly reversibly modified, as in 2'-O-methyl, 2'-deoxy-2'-fluoro, and 2',3'-dideoxynucleoside derivatives, or reversibly protected to allow a 3'-phosphoramidite to be prepared and used in standard chemical RNA synthesis, such as 2'-O-allyl, 2'-silyl, and 2'-O-thionocarbamate [Dellinger, D. J., Timar, Z., Myerson, J., Sierzchala, A. B., Turner, J., Ferreira, F., Kupihar, Z., Dellinger, G., Hill, K. W., Powell, J. A., Sampson, J. R., Caruthers, M. H. (2011) Streamlined process for the chemical synthesis of RNA using 2'-O-thionocarbamate-protected nucleoside phosphoramidites in the solid phase. J. Am. Chem. Soc. dx.doi.org/10.1021/ja201561z] (see, for example and without limitation, protecting groups shown in FIG. 2).

Another purpose of the instant invention is to provide oligonucleotide analogs that incorporate one or more of these nonstandard nucleoside analogs.

Another purpose of the instant invention is to disclose that the heterocycles of the instant invention do indeed mitigate epimerization of the ribonucleoside analogs, something not obvious in earlier disclosures, and something not obvious based on other prior art.

Another purpose of the instant invention is to provide nucleoside analogs in protected form that are suitable as precursors for the non-enzymatic synthesis of these oligonucleotide analogs.

Another purpose of the instant invention is to provide various phosphorylated derivatives of the stated nucleoside analogs, including triphosphates, which have utility in various enzymatic processes for the synthesis of the oligonucleotide analogs stated above.

Another purpose of the instant invention is to provide the processes for use of the above described oligonucleotide analogs, in particular, those that allow RNA molecules to be used as templates for RNA-directed RNA polymerases and reverse transcriptases.

Another purpose of the instant invention is to provide nonstandard nucleobases that are easily incorporated by RNA polymerases into the products of template-driven oligonucleotide synthesis. Various analyses of the interaction between polymerases and their substrates suggest that the polymerase seeks two unshared pairs of electrons in the minor groove, at position 3 of the purine (or analog) and at position 2 of the pyrimidine (or analog) [Steitz, T. in Burnett, R. M. and Vogel, H. J. (eds.) *Biological Organization: Macromolecular Interactions at High Resolution*; Academic Press: New York, 1987, pp. 45-55]. In addition, the base pairs that form three hydrogen bonds are expected to contribute more to duplex stability than pairs joined by just two hydrogen bonds.

These conditions are fulfilled for the compounds disclosed herein for implementing the pyDDA hydrogen bonding pattern.

BRIEF DESCRIPTION OF THE DRAWINGS

FIG. 2. The nucleobases of the instant invention with a variety of 2'-O blocking units.

DESCRIPTION OF INVENTION

Figure 1:
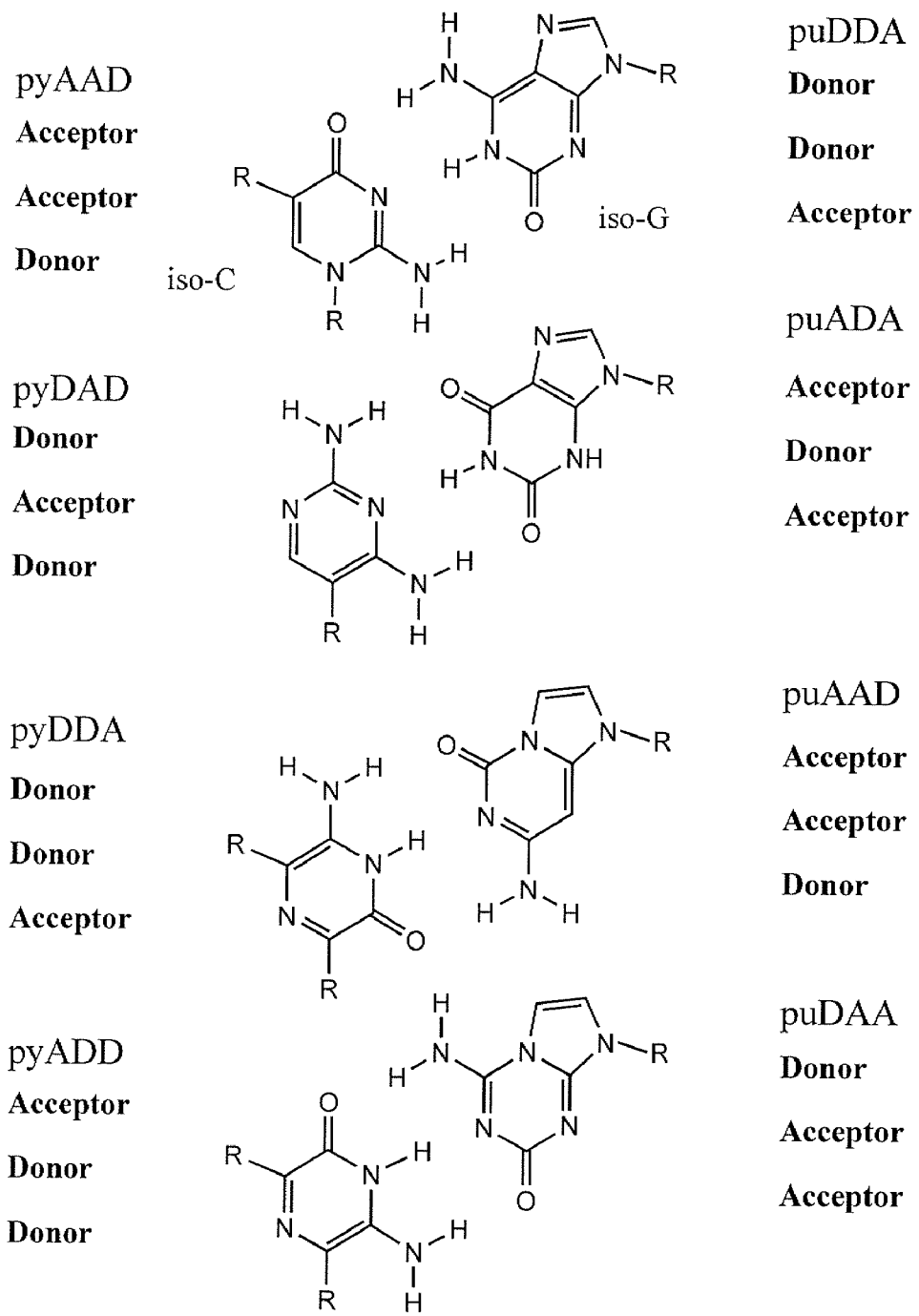
FIG. 1. From U.S. Pat. No. 6,140,496, the specific compositions of matter used to implement different hydrogen bonding patterns of the expanded genetic alphabet.

In the prior art, it was noted that the pyDDA hydrogen bonding pattern can be achieved in an uncharged species only with a C-glycoside, where the heterocycle is coupled to the sugar moiety by a C—C bond. The C-glycoside structure is different from the "N-glycosidic" structure found in the standard nucleosides, where the heterocycle is coupled to the sugar moiety by a C—N bond.

A special feature of C-nucleosides is their susceptibility to epimerization if an electron donating substituent is present in a suitable position on the heterocycle. This phenomenon was described for pseudouridine several decades ago [Cohn, W. E. (1960) *J. Biol. Chem.* 235, 1488.] and for other C-nucleosides since [Chambers, R. W.; Kurkov, V.; Shapiro, R. (1963) *Biochemistry*, 2, 1192.].

In the Benner laboratory, it was shown that C-nucleosides displaying the pyDDA hydrogen bonding pattern, and with 5'- and 3'-hydroxyls epimerize, usually in either acidic or basic medium, to a mixture of four isomers with the pyranose forms being the most abundant [Voegel, J. J.; Benner, S. A. (1994) *J. Am. Chem. Soc.* 116, 6929.] [von Krosigk, U.; Benner, S. A. (1995) *J. Am. Chem. Soc.* 117, 5361] [Voegel, J. J.; Benner, S. A. (1996) *Helv. Chim. Acta* 79, 1863]. With the hydroxyls protected or substituted, the epimerization limits itself to the α/β-forms of the furanoses. This epimerization is problematic, especially during the acidic deprotection step of the 5'-position during solid phase oligonucleotide synthesis. Further, the C-nucleoside, both in solution and when incorporated into an oligonucleotide, will also epimerize upon standing at pH 7 for a prolonged period of time. Analogous epimerization was observed in ribonucleosides with analogous heterocycles as nucleobase analogs [von Krosigk, U., Benner, S. A. (1995) pH-independent triple helix formation by an oligonucleotide containing a pyrazine donor-donor-acceptor base. *J. Am. Chem. Soc.* 117, 5361-5362].

The epimerization of pyDDA nucleoside analogs based on pyrazine heterocyclic systems caused these nucleobase analogs to have severely diminished utility.

While not wishing to be bound by theory, is was noted that the epimerization is specific acid catalyzed. Therefore, the rate of epimerization might be reduced by adjusting the electronic distribution in the heterocyclic ring. By further reasoning, an electron withdrawing group on the 5-position (where the numbering system used is defined to highlight the analogy to pyrimidine nucleosides, even in cases where the position of heteroatoms in the heterocyclic ring would cause the IUPAC numbering to be different) would draw the electrons away, so that they do not push the furanose ring system open, the first step in the epimerization process. A substituent at this position would not interfere with Watson-Crick pairing, nor with acceptance by polymerases and reverse transcriptases. Further, the electron withdrawing group would make the heterocycle less basic and less susceptible to oxidation than the pyridine heterocycle, making the second nitrogen in the pyrazine ring unnecessary for these purposes.

A survey of the prior art found no literature prior to the filing of the earliest applications for which priority is claimed that taught that the addition of an electron withdrawing group to a pyridine heterocycle would support the pyDDA and pyADD hydrogen bonding patterns of an artificially expanded genetic information system.

In principle, any of a number of electron withdrawing groups are conceivable for this purpose. Three of these are presently preferred, the cyano group, the nitro group, and an uncharged derivative of a carboxylic acid (an ester or amide). Also preferred are the cyano, carboxyl ester, or a carboxamido unit via an unsaturated linker (double or triple bond). The ester and amino groups have special value if appending a functional group is desired (e.g., a fluorescent group, a fluorescence quenching group, a metal liganding group, a catalytically active group, a group for binding to another species, or a group for capturing the oligonucleotide analog to a solid support) be desired at this site.

Further, no art, patent or other, appears to provide detailed procedures for the preparation of ribonucleosides carrying the heterocycles of the instant invention.

Further, none of these structures are covered by claims in the prior patent literature, other than those for which priority is claimed, or structures in the literature, other than that published by one of the inventors less than a year prior to the provisional patent whose priority date the instant application claims. Thus, the 4-amino-pyridine-2-one, 2-amino-pyridine-4-one, and 2,4-diaminopyridine heterocycles fall within the claim structures, and while these structures included the attachment of substituents at position 5, this substituents was designated to be an alkyl substituent. Neither the cyano group, the nitro group, nor an uncharged derivative of a carboxylic acid (an ester or amide) were included within the structures claimed, nor were the cyano, carboxyl ester, or a carboxamido unit via an unsaturated linker (double or triple bond) included. Nor were the structures nor their utility taught in the prior patents.

It is taught that the nucleobase analogs of the instant invention can be used as a component of an oligonucleotide to bind to a complementary oligonucleotide, where a nucleobase analog in the complementary oligonucleotide is complementary, according to the expanded Watson-Crick rules to the nucleobase analog of the instant invention. Further, it is taught that the nucleobase analogs of the instant invention can be used in oligonucleotide analogs containing a full range of other nucleobases and nucleobase analogs, either those in the literature or improvements as may emerge from time to time, implementing (in the extreme case) a full 12 letter genetic alphabet.

The synthesis of the nucleoside analogs of the instant invention uses as a key step the Heck coupling of a iodinated heterocycle with the non-standard hydrogen bonding pattern to 3-tertbutyldiphenylsilyloxy-2-hydroxymethyl-2,3-dihydrofuran, which is known in the literature, and referred to here as simply the "glycal" [Ireland, R. E., Thaisrivongs, S., Vanier, N., Wilcox, C. S. (1980) *J. Org. Chem.* 45, 48] [Larsen, E., Jorgensen, P. T., Sofan, M. A, Pedersen, E. B. (1994) *Synthesis*, 1037] [Walker II, J. A., Chen, J. J., Wise, D. S., Townsend, L. B. (1996) *J. Org. Chem.* 61, 2219] [Cameron, M. A.; Cush, S. B.; Hammer, R. P. (1997) *J. Org. Chem.* 62, 9065.] [Hutter, D., Benner, S. A. (2003) Expanding the genetic alphabet. Non-epimerizing nucleoside with the pyDDA hydrogen bonding pattern. *J. Org. Chem.* 68, 9839-9842].

The iodinated heterocycles to prepare the pyDDA and pyADD analogs of the instant invention are themselves prepared from the appropriate precursor pyridinones. Two routes, both well exemplified in the literature, are available to prepare these precursor pyridinones. In one route, the amino-3-pyridine bearing the electron withdrawing group is via a Katada rearrangement of the corresponding N-oxide, which is obtained by oxidizing the pyridine with mCPBA [Deady, L. W. (1977) *Synth. Commun.* 509.] [Daeniker, H. U., Druey, J. (1958) *Helv. Chim. Acta* 41, 2148.] [Taylor, E. C., Driscoll, J. S. (1960) *J. Org. Chem.* 25, 1716] [Markgraf, J. H., Brown, Jr., H. B., Mohr, S. C, Peterson, R. G. (1962) *J. Am. Chem. Soc.* 85, 958.] [McKillop, A., Bhagrath, M. K. (1985) *Heterocycles* 23, 1697.] [Sato, N., Miwa, N., Suzuki, H., Sakakibara, T. (1994) *J. Heterocyclic Chem.* 31, 1229.].

The second route [Hutter, D., Benner, S. A. (2003) Expanding the genetic alphabet. Non-epimerizing nucleoside with the pyDDA hydrogen bonding pattern. *J. Org. Chem.* 68, 9839-9842] starts with a 2,6-dichloropyridine derivative bearing the electron withdrawing group at the 3-position (e.g., the commercial 2,6-dichloro-3-nitropyridine). Aminolysis gives the corresponding aminochloropyridine derivative [Radl, S., Hradil, P. (1991) *Coll. Czech. Chem. Commun.* 56, 2420.]. This is hydrolyzed to the aminopyridone derivative with aqueous sodium hydroxide.

The appropriate aminopyridone bearing an electron group is then converted to the iodo heterocycle for coupling to the glycal. This is accomplished via iodination at the 5-position with N-iodosuccinimide (NIS) in DMF.

The Heck coupling is done following literature procedures, using palladium acetate with triphenylarsine as the catalyst system, and anhydrous dimethylformamide (DMF) as the solvent. The coupling to the glycal and subsequent deprotection and reduction have been reported previously by several groups [Farr, R. N., Outten, R. A. Cheng, J. C.-Y. Daves, Jr., G. D. (1990) *Organometallics* 9, 3151] [Zhang, H.-C., Daves, Jr., G. D. (1992) *J. Org. Chem.* 57, 4690] [Zhang, H.-C. Daves, Jr., G. D. (1993) *Organometallics* 12, 1499.] [Hsieh, H.-P. McLaughlin, L. W. (1995) *J. Org. Chem.*, 60, 5356] [Chen, D. L. McLaughlin, L. W. (2000) *J. Org. Chem.*, 65, 7468.] [Searls, T., Chen, D. L., Lan, T., McLaughlin, L. W. (2000) *Biochemistry*, 39, 4375] [Lan, T.; McLaughlin, L. W. (2001) *Bioorg. Chem.* 29, 198.] [Coleman, R. S., Madaras, M. L. (1998) *J. Org. Chem.* 63, 5700]. Triethylamine is often used instead of tributylamine as the base, since it is easier to remove during purification. Ca. 1.2 equivalents of glycal are used. After several days at 60° C., the β-nucleoside is obtained. The bulky TBDPS group at the 3'-position is assumed to direct addition of the heterocycle to the β-face This coupling generally creates the 2'-deoxy analog directly. However, special steps must be taken to generate the ribonucleoside analog. These involve the inventive sequence shown in the Figure and reported in the example. Here, the 2'-OH group is protected as an acetate. However, as intermediate 5 is fully protected other than in its 2'-OH unit, any protecting group desired for subsequent RNA synthesis is conceivable by introducing the appropriate electrophile to prepare, for example and without limitation, the 2'-O-allyl, 2'-silyl and 2'O-thionocarbamate derivatives [Dellinger, D. J., Timar, Z., Myerson, J., Sierzchala, A. B., Turner, J., Ferreira, F., Kupihar, Z., Dellinger, G., Hill, K. W., Powell, J. A., Sampson, J. R., Caruthers, M. H. (2011) Streamlined process for the chemical synthesis of RNA using 2'-O-thionocarbamate-protected nucleoside phosphoramidites in the solid phase. *J. Am. Chem. Soc.* dx.doi.org/10.1021/ja201561z].

Finally, the puAAD hydrogen bonding pattern may be implemented on the 5-aza-7-deazaguanosine heterocycle to provide the unshared pair of electrons in the minor groove believed to be important for polymerase recognition [Steitz, T. in Burnett, R. M. and Vogel, H. J. (eds.) *Biological Organization: Macromolecular Interactions at High Resolution*; Academic Press: New York, 1987, pp. 45-55.]. Synthetic routes to the ribonucleoside analogs bearing this nucleobase are also provided.

EXAMPLES

Example 1

Figure 3:
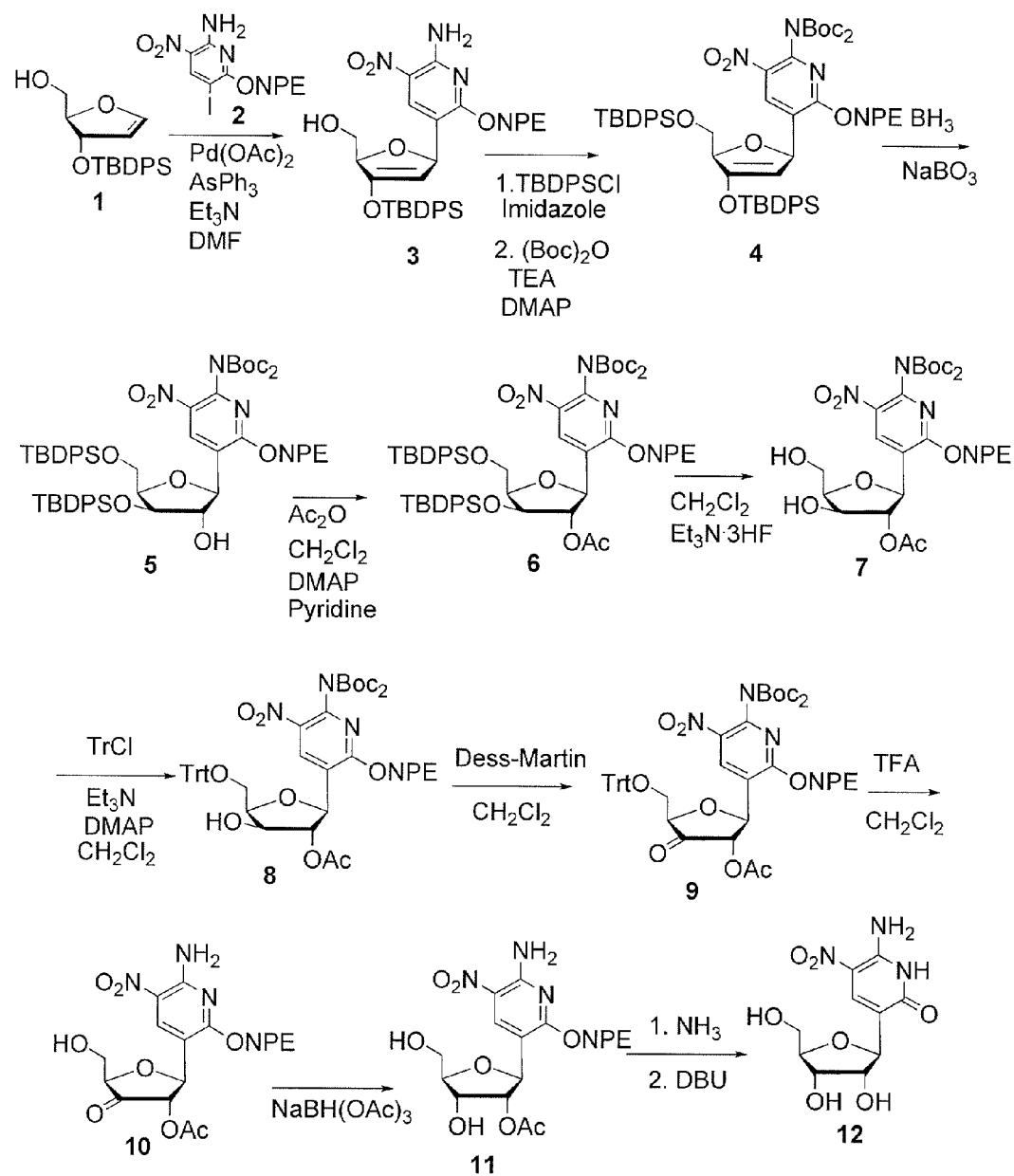
FIG. 3. Schematic showing the synthesis of the ribonucleoside analog carrying a nucleobase implementing the hydrogen bond donor-donor-acceptor pattern on a small heterocycle (pyDDA).

Preparation of the Ribonucleoside Analogs Carrying a Heterocycle that Implements the pyDDA Hydrogen Bonding Pattern Compound Numbers Make Reference to FIG. 3

Compound 3 (5-[2',5'-Dihydro-5'-(hydroxymethyl)-3'-[(1,1-dimethylethyl)diphenylsilyl]oxy-2'-furanyl]-3-nitro-6-[2-(4-nitrophenyl)ethoxy]-2-pyridinamine)

A mixture of triphenylarsine (146 mg, 0.476 mmol) and palladium acetate (53 mg, 0.238 mmol) in DMF (10 mL) was stirred at rt for 30 min. It was added to a mixture of glycal (compound 1, 930 mg, 2.62 mmol), compound 2 (1.025 g, 2.39 mmol), and triethylamine (0.66 mL, 4.77 mmol) in DMF (10 mL) and the resulting mixture was stirred at 70° C. for 18 hrs. It was poured into water (100 mL) and extracted with ethyl acetate. The combined organic layer was dried over $Na_2SO_4$, filtered and concentrated. The residue was purified by flash chromatography (silica gel, ethyl acetate:hexanes=1:2 to 1:1) to give a yellow solid (1.03 g, 66%).

Compound 4 (N,N-Bis[(1,1-dimethylethoxy)carbonyl]-5-[2',5'-dihydro-5'-[[[(1,1-dimethylethyl)diphenylsilyl]oxy]methyl]-3'-[(1,1-dimethylethyl)diphenylsilyl]oxy-2'-furanyl]-3-nitro-6-[2-(4-nitrophenyl)ethoxy]-2-pyridinamine)

A mixture of compound 3 (1.03 g, 1.58 mmol), TBDPSCl (0.62 mL, 2.5 mmol) and imidazole (340 mg, 5.0 mmol) in DMF (15 mL) was stirred at rt overnight. The mixture was poured into water and extracted with ethyl acetate. The organic layer was dried over $Na_2SO_4$, filtered and concentrated. The residue was purified by flash chromatography (silica, ethyl acetate:hexanes=1:2) to give a light yellow solid. It was mixed with di-tert-butyl dicarbonate (1.09 g, 5.0 mmol), triethylamine (1.25 mL, 9.0 mmol) and catalytic amount of DMAP (20 mg) in dichloromethane (30 mL). The mixture was stirred at rt for 1 h and washed with brine. The organic layer was dried over $Na_2SO_4$, filtered and concentrated. The residue was purified by flash chromatography (silica gel, ethyl acetate:hexanes=1:3) to give a light yellow solid. (1.38 g, 80%).

Compound 5 (N,N-Bis[(1,1-dimethylethoxy)carbonyl]-5-[3',5'-di-O-(tert-butyldiphenylsilyl)-β-D-xylofuranosyl]-3-nitro-6-[2-(4-nitrophenyl)ethoxy]-2-pyridinamine)

To a solution of compound 4 (1.38 g, 1.26 mmol) in THF (19 mL) was added borane-THF complex (1M in THF, 6.3 mL, 6.3 mmol) at 0° C. and slowly warmed to rt (over 2 or 3 hours) and stirred overnight. The mixture was quenched with water (1.5 mL) and stirred 5 min then treated with a sodium perborate (3.13 g) in water (9.4 mL) and stirred 2 h at rt. The mixture was diluted with brine and extracted with ethyl acetate. The combined organic layer was dried over $Na_2SO_4$, filtered and concentrated. The residue was purified by flash chromatography (silica gel, ethyl acetate:hexanes=1:3) to give a light yellow solid. (1.19 g, 85%)

Compound 6 (N,N-Bis [(1,1-dimethylethoxy)carbonyl]-5-[3',5'-di-O-(tert-butyldiphenylsilyl)-2'-O-acetyl-β-D-xylofuranosyl]-3-nitro-6-[2-(4-nitrophenyl)ethoxy]-2-pyridinamine)

A mixture of compound 5 (5.90 g, 5.3 mmol), acetic anhydride (1.8 mL, 10.06 mmol) and pyridine (1.7 mL) in dichloromethane (200 mL) was stirred at room temperature for 2 hours. The mixture was washed with water and concentrated. The residue was purified by flash chromatography (silica gel, ethyl acetate:hexanes=1:3) to give a light yellow solid. (5.5 g, 90%)

Compound 7 (N,N-Bis[(1,1-dimethylethoxy)carbonyl]-5-(2'-O-acetyl-β-D-xylofuranosyl)-3-nitro-6-[2-(4-nitrophenyl)ethoxy]-2-pyridinamine)

A mixture of compound 6 (1.15 g, 1.0 mmol), triethylamine trihydroflouride (4.9 mL, 30 mmol) and triethylamine (4 mL) in THF (40 mL) was stirred at room temperature for 2 days. The mixture was poured into water (100 mL) and extracted with ethyl acetate.

The combined organic layer was dried over $Na_2SO_4$, filtered and concentrated. The residue was purified by flash chromatography (silica gel, ethyl acetate:hexanes=2:1) to give a white solid. (530 mg, 78%)

Compound 8 (N,N-Bis[(1,1-dimethylethoxy)carbonyl]-5-(5'-O-trityl-2'-O-acetyl-β-D-xylofuranosyl)-3-nitro-6-[2-(4-nitrophenyl)ethoxy]-2-pyridinamine)

To a mixture of compound 7 (580 mg, 0.855 mmol), triethylamine (0.24 mL) and dimethylaminopyridine (5 mg) in dichloromethane (30 mL) was added trityl chloride (250 mg, 0.897 mmol) and the mixture was stirred at room temperature for 3 hours. The mixture was poured into water (100 mL) and extracted with dichloromethane. The combined organic layer was dried over $Na_2SO_4$, filtered and concentrated. The residue was purified by flash chromatography (silica gel, ethyl acetate:hexanes=1:2) to give a white solid. (670 mg, 85%)

Compound 9 (N,N-Bis [(1,1-dimethylethoxy)carbonyl]-5-(5'-trityl-3'-deoxy-3'-O-acetyl-β-D-ribofuranosyl)-3-nitro-6-[2-(4-nitrophenyl)ethoxy]-2-pyridinamine)

A mixture of compound 8 (460 mg, 0.5 mmol) and Dess-Martin periodinane (3.3 mL, 1.0 mmol, 0.3M solution in dichloromethane) in dichloromethane (20 mL) was stirred at room temperature for 1 hour. The mixture was filtered through Celite and the filtrate was washed with aqueous sodium bicarbonate. It was evaporated and the residue was purified by flash chromatography (silica gel, ethyl acetate:hexanes=1:2) to give a white solid. (370 mg, 80%)

Compound 10 (5-(3'-Deoxy-3'-oxo-2'-O-acetyl-β-D-ribofuranosyl)-3-nitro-6-[2-(4-nitrophenyl)ethoxy]-2-pyridinamine)

To a solution of compound 9 (370 mg, 0.40 mmol) in dichloromethane (10 mL) was added trifluoroacetic acid (0.2 mL) and the mixture was stirred at room temperature for 2 hours. The mixture was neutralized by aqueous sodium bicarbonate and mixed with water and extracted with dichloromethane. The combined organic layer was dried over $Na_2SO_4$, filtered and concentrated. The residue was purified by flash chromatography (silica gel, ethyl acetate:hexanes=3:2) to give a yellow solid. (144 mg, 75%)

Compound 11 ((2'-O-Acetyl-β-D-ribofuranosyl)-3-nitro-6-[2-(4-nitrophenyl)ethoxy]-2-pyridinamine)

To a solution of compound 10 (476 mg, 1.00 mmol) in acetic acid (10 mL) and acetonitrile (10 mL) was added sodium triacetoxyborohydride (635 mg, 3.00 mmol) at 0° C. and stirred for 1 h. It was poured into water and extracted with ethyl acetate. The combined organic layer was dried over $Na_2SO_4$, filtered and concentrated. The residue was purified by flash chromatography (silica gel, ethyl acetate:hexanes=2:1 to 100% ethyl acetate) to give a light yellow solid. (332 mg, 70%)

Compound 12 (6-Amino-3-β-D-ribofuranosyl-5-nitro-2(1H)-pyridone)

To a solution of compound 11 (47 mg, 0.10 mmol) in methanol (2 mL) was added ammonium hydroxide (0.5 mL) at room temperature and stirred for 1 h. It was poured into water and extracted with ethyl acetate. The combined organic layer was dried over $Na_2SO_4$, filtered and concentrated. The residue was dissolved in acetonitrile (2.5 mL) and treated with DBU (0.1 mL) and the mixture was stirred at room temperature overnight and evaporated. The residue was purified by flash chromatography (silica gel, $CH_2Cl_2$:MeOH=5:1 to 2:1) to give a yellow solid. (20 mg, 70%)

Example 2

Figure 4:
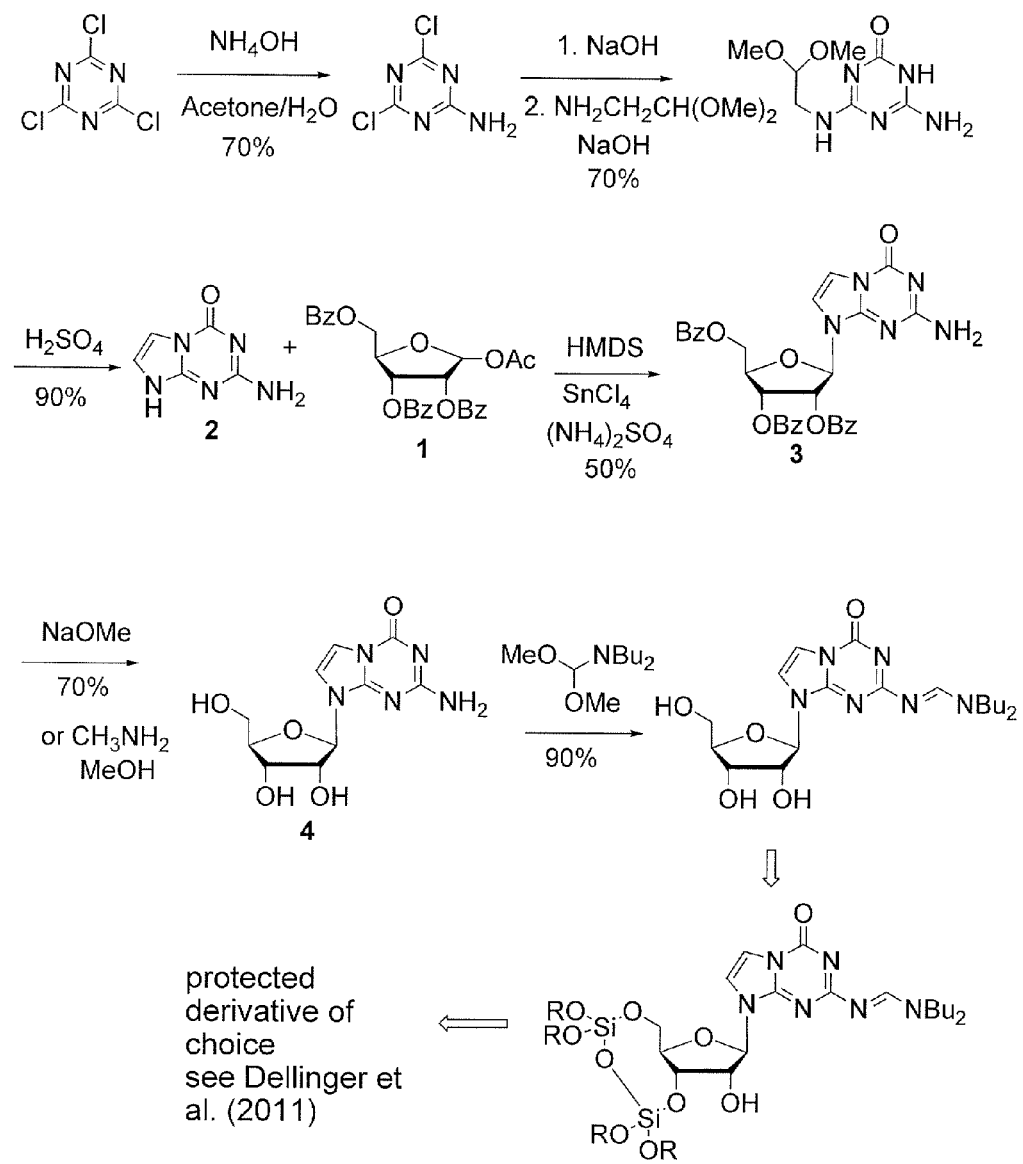
FIG. 4. Schematic showing the synthesis of the ribonucleoside analog carrying a nucleobase implementing the hydrogen bond acceptor-acceptor-donor pattern on a large heterocycle (puAAD).
Figure 5:
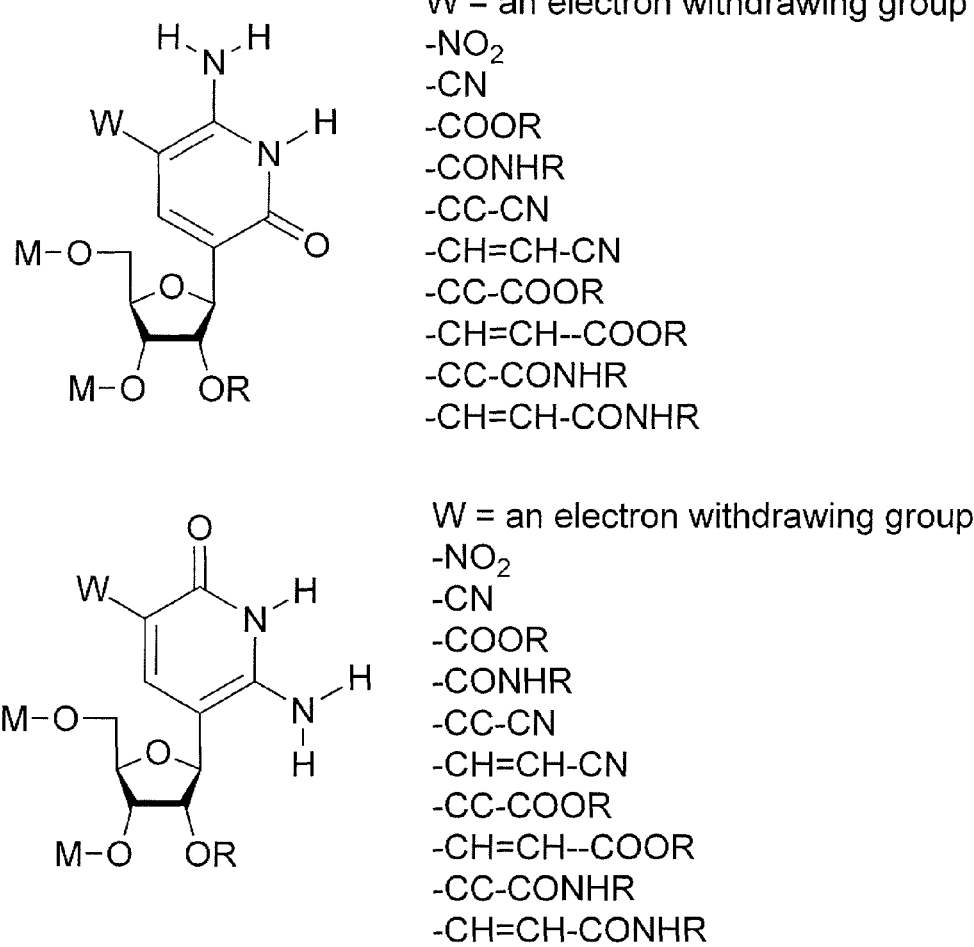
FIG. 5. Alternative electron withdrawing groups to provide compounds of the instant invention with their desired properties.

Synthesis of a Ribonucleoside Analog Implementing the puAAD Hydrogen Bonding Pattern Compound Numbers Make Reference to FIG. 4

Compound 3 (2-Amino-8-(2,3,5-tri-O-benzoyl-β-D-ribofuranosyl)-imidazo[1,2-a]-s-triazin-4-one). A mixture of 2 (7.55 g, 50 mmol), freshly distilled hexamethyldisilazane (38 mL), and a few crystals of ammonium sulfate (50 mg) was heated at reflux temperature for 15 h with the exclusion of moisture. The excess hexamethyldisilazane was removed by distillation and the residual gum was dissolved in anhydrous 1,2-dichloroethane (250 mL). To the solution was added compound 1 (25.22 g, 50 mmol) followed by stannic chloride (17.5 g, 67.5 mmol). The reaction mixture was protected from moisture and stirred for 30 h at room temperature. The brown solution was then poured into 500 mL of chloroform and the resulting emulsion was filtered through Celite. The filtrate was washed with water, dried over anhydrous sodium sulfate and evaporated. The residue was purified by column chromatography (silica gel, ethyl acetate:water:1-propanol=4:2:1, v/v, upper phase) to give a light yellow solid. (17.0 g, 56%).

Compound 4 (2-Amino-8-β-D-ribofuranosyl-imidazo[1,2-a]-s-triazin-4-one)

A mixture of 3 (6.04 g, 10 mmol) and methylamine (20 mL, 40% solution in water) in methanol (200 mL) was stirred at room temperature overnight. The total volume was reduced to half by rotary evaporation. Ethyl ether (200 mL) was added to the mixture. The resulting solid was filtered and washed with ether and dried to give a white solid. (2.0 g, 70%).

Example 3

Making a Protected Derivative of the pyDAD Nucleoside of the Instant Invention Suitable for Use in Automated RNA Synthesis Tritylation The protected nucleoside analog (8.7 mmol) having preselected 2'-O blocking group, is dissolved in dry pyridine (150 mL). To the solution was added 4',4"-dimethoxytrityl chloride (1.2 equiv). The reaction mixture was stirred at room temperature for 24 hours. The reaction was quenched by the addition of water (3 mL). The solution is concentrated under vacuum, and an aqueous solution of $NaHCO_3$ (80 ml) was added. The mixture is extracted with EtOAc, dried ($Na_2SO_4$), the solvents are evaporated under reduced pressure, and the product is isolated by column chromatography (chloroform/acetone 9:1, then 9:2).

Phosphoramidite.

The protected derivative from above (0.12 mmol) is dissolved in $CH_3CN$ (2.0 mL). The solution is then treated with bis-(N,N-diisopropylamino)-3-cyanoethyloxyphosphine (Aldrich, 1.2 equiv.), and diisopropylammonium tetrazolide (0.06 mmol), following a literature procedure [McBride, L. J., Kierzek, R., Beaucage, S. L. & Caruthers, M. H. (1986) *J. Am. Chem. Soc.* 108, 2040-2048]. The progress of the reaction is monitored by TLC ($SiO_2$ eluted with EtOAc:$CH_2Cl_2$:triethylamine 45:45:10). An additional portion (0.02 mL) of bis-(N,N-diisopropylamino)-3-cyanoethyloxyphosphine is then added, and stirring continued for an additional hour. Water (2 drops) is added, the mixture stirred for 15 min, the mixture diluted with $CH_2Cl_2$ (30 mL), and the organic layer washed with aqueous $Na_2CO_3$ (2%) and dried ($Na_2SO_4$). The phosphoramidite (120.3 mg, 93%) is isolated by chromatography ($SiO_2$, EtOAc:$CH_2Cl_2$:triethylamine 45:45:10 as eluant).

Example 4

Synthesis of the Triphosphate of the Analog Implementing the pyDDA Hydrogen Bonding Pattern 3'-O-(Acetyl) Derivative of the Nucleoside Analog The dimethoxytritylated nucleoside analog from above (0.200 mmol) is coevaporated with dry pyridine (0.8 mL). The residue was redissolved in pyridine (1 mL) under dry Ar. Acetic acid anhydride (10 equiv) is added dropwise, and the reaction mixture is stirred for 3 h. The solution is then cooled on an ice bath, and the reaction is quenched by addition of methanol (1 mL). The solvents are evaporated under reduced pressure. The remaining foam is coevaporated with dry toluene (1 mL), and the residue is dissolved in a mixture of trifluoroacetic acid and $CH_2Cl_2$ (2% v/v, 10 mL total volume). The mixture is then stirred for 30 min, at which point saturated aqueous $NaHCO_3$ solution (5 mL) is added. The phases are separated, the aqueous phase isolated, and the aqueous phase extracted with $CH_2Cl_2$. The combined organic phases are concentrated under reduced pressure, and the remaining yellowish oil is resolved by chromatography on silica gel ($CH_2Cl_2$/MeOH 98:2) to afford the 3'-O-acetyl derivative of the nucleoside, with its 5'-OH group free.

5'-O-Triphosphate Derivative of the Nucleoside Analog

The 3'-acetylated nucleoside analog (0.162 mmol) is then coevaporated again with dry pyridine (1 mL). The residue is then redissolved in a mixture of dry pyridine (162 µL) and dry 1,4-dioxane (486 µL) under Ar. A freshly prepared solution of 2-chloro-4H-1,3,2-benzodioxaphosphorin-4-one (1 M) in 1,4-dioxane (162 µL, 1.0 equiv) is then added to the stirred reaction mixture. A white precipitate forms immediately. After 10 minutes, a well vortexed emulsion of tributylammonium pyrophosphate (110 mg) in DMF/tri-n-butylamine (3:1, 648 µL) is quickly added. This causes the precipitate to dissolve immediately.

After 10 minutes of incubation at room temperature, a 1% solution of iodine in pyridine/water (98:2, 3.24 mL) is added dropwise. After 15 min following completed addition of the iodine solution, the solvents are removed at 40° C. under reduced pressure. The remaining brown oil is dissolved in water/MeOH (1:1, 10 mL), and the mixture is allowed to stand for 30 minutes. Then, a portion of solution of aqueous concentrated ammonia (20 mL) is added; the solution turns turbid. The suspension is stirred for 1 h, the solvents are removed at 40° C. under reduced pressure, and the remaining light brown oil is coevaporated with water.

Water/acetonitrile (95:5, 2 mL) is then added to yield a light brown suspension. The unsoluble components are removed by filtration (0.2µ cellulose acetate membrane) to yield a clear, slightly yellow, filtrate containing the triphosphate. The triphosphate is purified by chromatography (DEAE Sephadex, 30 mL, 1.5×18 cm; TEAB 0.1 M to 0.8 M (linear gradient) in the presence of 10% acetonitrile). Further purification is done by reversed phase RP-HPLC (Column: Nova-Pak HR C18 cartridge (Waters), 6µ, 25×100 mm. Solvent A: triethylammonium acetate (25 mM, pH 7.0); solvent B: acetonitrile. Flow rate: 5.5 mL/min. Gradient: 0-1 min 100% A; 10 min 13% B (linear); 55 min 18% B (linear)). The eluate is lyophilized to dryness, and the residue is redissolved in water. Dissolution and lyophilization are done three more times, to remove the residual triethylamonnium acetate. The triphosphate is stored at −20° C., either as 5 mM solution in water or as a lyophilized powder. The triphosphate can be recognized by characteristic signals in the $^{31}$P NMR in $D_2O$ solvent (121 MHz: δ relative to phosphoric acid=−7.9 (poorly resolved doublet), −9.1 (doublet), and −20.6 (triplet) ppm).

What is claimed is:

1. A compound having the structure

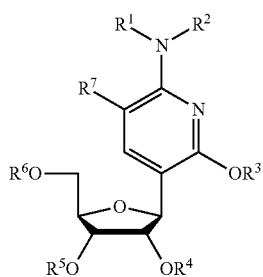

wherein $R^1$ and $R^2$ are independently selected from the group consisting of —H, —CO—X, and

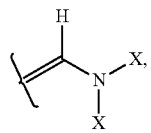

$R^3$ is independently selected from the group consisting of —$CH_2$—$CH_2$—$NO_2$, —$CH_2$—$CH_2$—CN, and —$CH_2$—$CH_2$-phenyl-$NO_2$, $R^4$ is independently selected from the group consisting of —X, —CO—X, $CH_2$—$CH_2$=$CH_2$, —$SiX_3$, —$CH_2$—O—$CH_2$-phenyl-$NO_2$, —$CH_2$—O—$CH_2$—$CH_2$—$SO_2$-aryl, —$CH_2$—O—$CH_x$—$CH_2$—CN, —$CH_2$—O—$CH_2$—$CH_2$—CN, levulinyl, —$CH_2$—SS—X, and

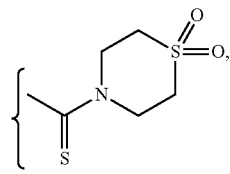

$R^5$ is —P—($NQ_2$)O—$CH_2$—$CH_2$—CN, wherein Q is an alkyl group, $R^6$ is independently selected from the group consisting of trityl, methoxytrityl, dimethoxytrityl, and trimethoxytrityl, $R^7$ is independently selected from the group consisting of —$NO_2$, —CN, —COOR, —CONHR, —CH=CH—CN, —CH=CH—COOR, —CH=CH—CONHR, —CC—CN, —CC—COOR, and —CC—CONHR, wherein R is independently selected from the group consisting of an alkyl group, an aryl group, and an alkyl group further substituted by a protected amino group, a protected carboxyl group, or a protected imidazolyl group, and X is a group independently selected from the group consisting of —H, -alkyl, -alkaryl, aryl, and aralkyl; with the proviso that, in the definition of substituent —$SiX_3$, the variable X cannot be H.

2. The compound of claim 1 wherein $R^1$ is H and $R^2$ is CO—$CH_3$.

3. The compound of claim 1 wherein $R^3$ $CH_2$—$CH_2$-phenyl-$NO_2$.

4. The compound of claim 1 wherein $R^4$ is tert-butyldimethylsilyl.

5. An oligonucleotide where at least one of the nucleotide units is replaced by a nucleoside analog having the following structure:

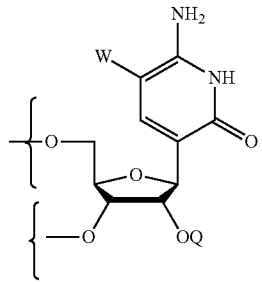

wherein Q is independently selected from the group consisting of H, methyl, allyl, and alkyl, and W is independently selected from the group consisting of —$NO_2$, —CN, —COOR, —CONHR, —CH=CH—CN, —CH=CH—COOR, —CH=CH—CONHR, —CC—CN, —CC—COOR, and —CC—CONHR, wherein R is selected from the group consisting of an alkyl group, an aryl group, and an alkyl group further substituted by a protected amino group, a protected carboxyl group, or a protected imidazolyl group.

6. The compound of claim 5 wherein Q is methyl.

7. The compound of claim 5 wherein Q is H and W is —$NO_2$.

8. The compound of claim 5 wherein Q is H and W is —CN.

9. The compound of claim 5 wherein Q is methyl and W is —$NO_2$.

10. The compound of claim 5 wherein Q is methyl and W is —CN.

11. The compound of claim 5 wherein Q is H.

* * * * *